(12) United States Patent
Hochgraeber et al.

(10) Patent No.: US 9,945,501 B2
(45) Date of Patent: *Apr. 17, 2018

(54) PLUG UNIT AND CONNECTION SYSTEM FOR CONNECTING CAPILLARY TUBES

(71) Applicant: DIONEX SOFTRON GMBH, Germering (DE)

(72) Inventors: Hermann Hochgraeber, Offenberg (DE); Adolf Satzinger, Olching (DE)

(73) Assignee: DIONEX SOFTRON GMBH, Germering (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/819,743

(22) Filed: Aug. 6, 2015

(65) Prior Publication Data

US 2015/0338000 A1 Nov. 26, 2015

Related U.S. Application Data

(63) Continuation of application No. 13/132,578, filed as application No. PCT/DE2009/001688 on Nov. 27, 2009, now Pat. No. 9,134,283.

(30) Foreign Application Priority Data

Dec. 2, 2008 (DE) .......... 10 2008 059 897

(51) Int. Cl.
*F16L 19/06* (2006.01)
*F16L 21/04* (2006.01)
(Continued)

(52) U.S. Cl.
CPC .............. *F16L 21/04* (2013.01); *F16L 19/00* (2013.01); *F16L 19/061* (2013.01);
(Continued)

(58) Field of Classification Search
CPC .......... F16L 21/04; F16L 21/035; F16L 19/00; F16L 19/061
(Continued)

(56) References Cited

U.S. PATENT DOCUMENTS 1,121,386 A * 12/1914 Means .................. F16L 19/065
                                                  175/320
2,320,812 A *  6/1943 Cowles ................... F16L 19/04
                                                  285/353 X (Continued)

FOREIGN PATENT DOCUMENTS

| CN | 2087340 U | 10/1991 |
|---|---|---|
| WO | 9932821 | 7/1999 |
| WO | 2004018990 | 3/2004 |

OTHER PUBLICATIONS

PCT, International Search Report for PCT Application No. PCT/DE2009/001688 dated Apr. 9, 2010 (3 pages).

(Continued)

*Primary Examiner* — Gregory Binda
(74) *Attorney, Agent, or Firm* — Timothy J. Ohara

(57) ABSTRACT

A plug unit and system for connecting capillary tubes, especially for high-performance liquid chromatography, with a plug capillary tube projecting through a hole of a plug housing, which is detachably connectable to a bushing unit. The plug capillary tube front end projects into a capillary tube receptacle in the bushing unit with its end face essentially aligned opposite a front end of a bushing capillary tube or a bushing capillary tube opening of the bushing unit, the end face of which is butted against. The plug housing applies a force, with its end face facing the plug capillary tube end, directly or indirectly on an annular sealing element surrounding the plug capillary tube in the region of the front end of the plug capillary tube such that the front end of the plug capillary tube is sealed through deformation of the (Continued)

sealing element against the capillary tube receptacle opening.

6 Claims, 5 Drawing Sheets

(51) Int. Cl.
    *F16L 21/035*     (2006.01)
    *F16L 19/00*     (2006.01)
    *G01N 30/60*     (2006.01)

(52) U.S. Cl.
    CPC ........ *F16L 21/035* (2013.01); *G01N 30/6026* (2013.01); *G01N 30/6039* (2013.01); *G01N 30/6091* (2013.01)

(58) Field of Classification Search
    USPC .................................................. 285/234, 353
    See application file for complete search history.

(56) References Cited

U.S. PATENT DOCUMENTS

| | | |
|---|---|---|
| 3,880,452 A | 4/1975 | Fields |
| 4,083,702 A | 4/1978 | Hartigan et al. |
| 4,538,842 A | 9/1985 | Kowal et al. |
| 4,619,473 A | 10/1986 | Someya |
| 4,690,437 A | 9/1987 | Anderson, Jr. |
| 4,691,944 A * | 9/1987 | Viall, Jr. ............. F16L 19/0231 285/321 |
| 4,991,883 A | 2/1991 | Worden |
| 5,087,083 A * | 2/1992 | Usui ................... F16L 13/0236 |
| 5,190,523 A | 3/1993 | Lindmayer |
| 5,275,448 A | 1/1994 | McNaughton et al. |
| 6,273,478 B1 | 8/2001 | Benett et al. |
| 6,494,500 B1 | 12/2002 | Todosiev et al. |
| 7,404,581 B2 | 7/2008 | Baving et al. |
| 2004/0035774 A1 | 2/2004 | Horsman et al. |
| 2005/0011821 A1 | 1/2005 | Held et al. |
| 2005/0035598 A1 * | 2/2005 | Charles .................. B21K 21/12 285/353 |
| 2006/0213824 A1 | 9/2006 | Higgins et al. |
| 2015/0300542 A1 * | 10/2015 | Graham ............. G01N 30/6026 |

OTHER PUBLICATIONS

PCT, Written Opinion of the International Search Authority for PCT Application No. PCT/DE2009/001688 dated Apr. 9, 2010 (7 pages).

SIPO, First Notification of Office Action issued Jun. 8, 2013 in corresponding Chinese Patent Application No. 200980148433.9 (23 pages).

* cited by examiner

PLUG UNIT AND CONNECTION SYSTEM FOR CONNECTING CAPILLARY TUBES

CROSS-REFERENCE TO RELATED APPLICATIONS

This application is a Continuation under 35 U.S.C. § 120 and claims the priority benefit of U.S. application Ser. No. 13/132,578, filed Jul. 7, 2011, now U.S. Pat. No. 9,134,283, entitled "PLUG UNIT AND CONNECTION SYSTEM FOR CONNECTING CAPILLARY TUBES, ESPECIALLY FOR HIGH-PERFORMANCE LIQUID CHROMATOGRAPHY," which is the United States National Stage Application, under 35 U.S.C. § 371, of International Application PCT/DE2009/001688, filed Nov. 27, 2009, which claims the priority benefit to German Patent Application No. 10 2008 059 897.6, filed Dec. 2, 2008, which applications are hereby incorporated herein by reference in their entireties.

BACKGROUND OF THE INVENTION

Technical Field of the Invention

The invention relates to a plug unit for connecting capillary tubes, especially for high-performance liquid chromatography. In addition, the invention relates to a connection system consisting of a bushing unit and such a plug unit.

Description of Related Art

In chromatography systems, liquids or gases are fed through suitable connection lines between the components of the relevant system. These connection lines, which can be made, for example, from stainless steel, have suitable connection systems, also called fittings, available at their ends to enable creating a tight connection with the connectors of the components.

Such a connection system has already been described in 1975 in U.S. Pat. No. 3,880,452. A capillary tube forming the connection line between two components is here pushed into the capillary tube receptacle opening of a bushing unit or connection unit and fixed in the bushing by means of a threaded fastener that has a central hole for guiding the capillary tube. For sealing, one or more sealing elements that surround the capillary tube in their front end region are pressed into the capillary tube receptacle opening, which runs conically inward, by means of the threaded fastener when the capillary tube and bushing unit are connected.

However, it is disadvantageous that the sealing position is not realized in the plane of the end surface perpendicular to the longitudinal axis of the capillary tube, but is instead offset rearward a certain distance from the end face in the axial direction. In this way, a dead volume is produced that has a disadvantageous effect, especially in high-performance liquid chromatography. In order to be able to guarantee the tightness of such connections for the extremely high pressures used in high-performance liquid chromatography, sealing elements are often used like those described, for example, in U.S. Pat. No. 4,619,473 as prior art (FIG. 2). That publication involves annular sealing elements that are, for the most part, likewise made from stainless steel and that have, in longitudinal section, a conical profile of the outer diameter. Such a sealing element interacts with a conical receptacle opening in the bushing unit, wherein the conical receptacle opening has a larger angle than the sealing element relative to the longitudinal axis of the capillary tube. Here, when the sealing element is pressed into the receptacle opening, an extremely high, radially inward pressure is exerted by means of a threaded fastener onto the front region of the sealing element, so that the sealing position is realized. Through this pressure, however, a deformation of the sealing element and the capillary tube is usually generated, wherein the sealing element is pressed with its annular front edge into the outer periphery of the capillary tube. Such a deformation is undesired, especially because the sealing element is connected to the capillary tube here with a positive interference fit and non-positive-interference-fit connection and the sealing element can no longer be slipped onto the capillary tube easily in the axial direction. If the sealing connection is released and should such a plug element be screwed into another bushing unit, for example because a component of the chromatography system must be replaced, then a tight connection can indeed be produced, but due to tolerances or manufacture-dependent differences in the depth of the receptacle opening, it can no longer be guaranteed that the capillary tube will again apply a force with its end face onto the end face of the line to which it should connect. If the receptacle opening of the bushing unit of the exchanged component is longer in the axial direction than the previously used component, then an undesired dead volume is created. If the receptacle opening for the capillary tube in the exchanged component is shorter in the axial direction than the previously used component, then the capillary tube is actually deformed, possibly damaged, by the pressure of the threaded fastener, and a tight connection is no longer possible under some circumstances. This is because the sealing element mounted on the capillary tube with a positive interference fit and non-positive-interference-fit connection cannot move in the axial direction.

In the case of such a fitting, however, a small dead volume also can be rarely avoided if the end faces of the capillary tube and the line to be connected are directly opposite each other or contact each other, because the sealing position is not located in the region of the end face of the capillary tube or the line to be connected.

In order to be able to compensate for such tolerances or in order to be able to use connection systems of different manufacturers with one and the same plug unit, a self-adjusting plug for high-performance liquid chromatography is described in U.S. Pat. No. 6,494,500, in which the capillary tube is biased axially toward the capillary tube receptacle openings of the bushing unit by means of a spring provided in the threaded fastener. For the seal, however, a replaceable ferrule is used that again has a conical construction in its front region, and to form the seal interacts with an inner wall of the ferrule receptacle opening that has a more pronounced conical construction. Here there is again the risk that the ferrule is "crimped tight" onto the capillary tube, especially when the sealing element is made from a metal, for example, stainless steel.

In addition, in this plug unit it is disadvantageous that a support element for the helical spring must be mounted on the capillary tube, wherein this support element makes the production of such a plug unit more complicated.

For avoiding a dead volume, a unit is known from U.S. Pat. No. 4,083,702 for connecting capillary tubes for gas chromatography in which the capillary tubes are similarly connected butted to each other with their end faces. The capillary tubes are fixed by means of ring elements that have a wedge shape in the longitudinal section and that interact with corresponding, conical recesses in the connector housing. In this case, however, the seal is simpler relative to a connection that is compatible with high-performance liquid chromatography, since the pressures used for gas chromatography are significantly lower, for example, up to 6 bar.

In addition to the already mentioned disadvantages, the known connection systems feature the disadvantage that the risk arises that the sealing element will remain in place in the relevant receptacle opening of the bushing unit when the plug unit is removed and the capillary tube is pulled out from the bushing unit.

In addition, the trend in high-performance liquid chromatography is toward using thinner capillary tubes, since these can be more easily bent to better adapt them to the existing installation conditions. Due to the production process, thinner capillary tubes also feature smaller tolerances in the inner diameter and smaller eccentricity of the inner diameter. To allow using capillary tubes with smaller outer diameters in connection with conventional bushing units or connection units, the tubes are provided at the ends with a sleeve for adapting the outer diameter to the diameter of the thicker, conventional capillary tubes. This represents an additional expense, however, and increases the dead volume of a connection.

SUMMARY OF THE INVENTION

The invention provides a plug unit for connecting capillary tubes, especially for high-performance liquid chromatography, which can be used in a simple way for capillary tubes with different outer diameters in connection with bushing units with conventional diameters of receptacle openings. In addition, the present invention prevents the problem that, when the plug unit is removed, the sealing element detaches from the capillary tube and remains in the bushing unit. In addition, the invention provides a connection system with such a plug unit.

In accordance with the present invention, in a simple way, contact of the end face of the capillary tube against the end face of a capillary tube to be connected or against the end face of an opening of a fluid channel in a bushing unit can be guaranteed in that the capillary tube has on its front end, a force-receiving region projecting in the radial direction past the inner diameter of the annular sealing element. In this manner, the present invention ensures that, for the connection of the plug housing with the bushing unit, the plug housing applies a force with its end face on the sealing element and the sealing element consequently applies a force on the force-receiving region of the plug capillary tube with an axial contact force. In addition, the sealing element has a construction that can be deformed sufficiently elastically or plastically to simultaneously guarantee sealing of the plug capillary tube relative to the bushing unit or the capillary tube receptacle opening. The sealing is performed in the region of the radially outward extending force-receiving region of the plug capillary tube, so that a dead volume is avoided.

The force-receiving region advantageously has its greatest diameter in the plane of the end face of the plug capillary tube or in its direct vicinity, in order to prevent material of the sealing element from being pressed into an annular gap between the end face of the plug capillary tube and the end face of the bushing capillary tube or the floor of the receptacle opening in the bushing unit in which the bushing capillary tube opening is provided.

The thicker section provided at the front end of the plug capillary tube in the form of the force-receiving region guarantees that when the plug capillary tube is pulled out from the capillary tube receptacle opening when a connection system is disassembled, the sealing element is also removed. A later removal of the seal from the receptacle opening, possibly with a special extraction tool, is avoided.

In order to be able to use (thinner) capillary tubes with different thicknesses together with existing bushing units that were originally provided for thicker capillary tubes, only one suitable sealing element need be used with a suitable inner and outer diameter, as well as a plug housing with a matching axial hole for receiving the capillary tube. The additional use of adapter sleeves or the like is not required.

In addition, a plug unit constructed in this way according to the invention could also be used for conventional, known bushing units with different, manufacturer-dependent capillary tube receptacle opening hole depths. In such embodiments, only the plug housing must be provided with connection means that allow the secure connection in any position within a correspondingly large axial tolerance range. This can also be realized in a simple way by a thread, in particular, a fine thread. Obviously, the thread must be selected to match the bushing unit. For bushing units of known plug units, a UFN10-32 thread is usually used, however only thread that satisfies this condition or is suitable for this purpose.

For the use of a fine thread, that is, a thread with a very low pitch, it is also ensured that a high contact pressure could be exerted on the sealing element, in order to guarantee the required tightness even for the extremely high pressures used in high-performance liquid chromatography. The invention uses the fact that the system pressure active surface area, and thus also the force needed for sealing, is especially small when sealing at the base of the hole of the bushing unit.

According to one embodiment of the invention, the force-receiving region of the plug capillary tube can be constructed rotationally symmetric to the longitudinal axis and can advantageously have an outer diameter increasing continuously toward the end face of the plug capillary tube. For example, a trumpet-shaped or conical structure of a force-receiving region could be produced through simple compression of the front region of a capillary tube. A corresponding tool, however, should have a pin that engages in the channel opening of the capillary tube during the compression process, in order to maintain the inner diameter at the original value.

According to another embodiment, the force-receiving region of the plug capillary tube could have arms extending radially outward.

The sealing element advantageously has a hole for receiving the plug capillary tube that corresponds, in the assembled state, essentially to the outer diameter of the plug capillary tube. Advantageously, the sealing element could have an elastic construction, so that it surrounds the outer periphery of the plug capillary tube with a biasing tension directed radially inward in the assembled state.

To simplify applying it to the plug capillary tube, the sealing element could be constructed as a slotted ring element that has elasticity sufficient to allow it to be either pushed from the front onto the plug capillary tube or placed from the side onto the plug capillary tube.

The outer diameter of the sealing element advantageously is formed to be larger than the outer diameter of the force-receiving region of the plug capillary tube. In this manner, it can be guaranteed that a sealing effect is also realized in a region radially outside of the end face of the plug capillary tube, for example, by pressing the sealing element onto the floor of a corresponding receptacle opening in the bushing unit in a region radially outside of the end face of the plug capillary tube.

In such embodiments, the sealing element could be constructed so that it surrounds, with a positive interference fit, the force-receiving region of the plug capillary tube with its front region in the non-pressurized or no-tension state. The front end face of the sealing element, however, should not project past the end face of the plug capillary tube in the axial direction, in order to guarantee butted pressing of the end face of the plug capillary tube onto an opposite end face, and thus to avoid dead volume.

A pressure piece that has an axial hole in which the plug capillary tube is received could also be provided in the axial direction between the end face of the plug housing or a corresponding part of the plug housing and the sealing element. In such embodiments, the hole has an inner diameter that is only slightly greater than the outer diameter of the capillary tube, at least in a front region of the pressure piece. In this way it is avoided that, in the case of a high pressure being exerted by the pressure piece onto the sealing element, material of the sealing element enters into the annular gap between the outer diameter of the plug capillary and the inner diameter of the axial hole of the pressure piece. The use of a pressure piece offers the advantage that there is no friction between the sealing element and the pressure piece if a threaded connection is used between the plug housing and the bushing unit, and consequently damage to or negative effects on the sealing element during the assembly process are avoided. In addition, the use of a pressure piece allows the use of a uniform plug housing for different capillary tube diameters, wherein in this case only the pressure piece, which is simple to produce, must be adapted to the outer diameter of the capillary tube.

The invention will be explained in greater detail below with reference to the embodiments shown in the drawings.

DETAILED DESCRIPTION

Figure 1:
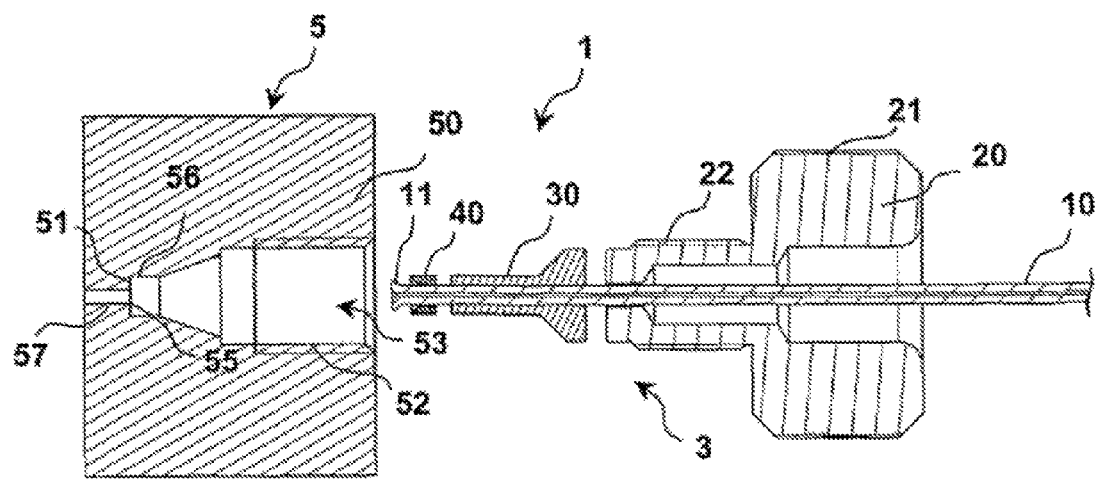
FIG. 1 shows a diagram of the components of a first embodiment of a connection system according to the invention, in a longitudinal section.

The connection system 1 shown in the disassembled state in FIG. 1 comprises a bushing unit 5, which is shown only schematically with respect to its outer contours that are not relevant to the invention, and which can be arranged, for example, on a component of a system for high-performance liquid chromatography, such as, for example, on a separating column. In addition, the connection system 1 comprises a plug unit 3. For its part, the plug unit 3 comprises, a plug capillary tube 10 that can be made, for example, from stainless steel, a plug housing 20 depicted in the form of a screw, a pressure piece 30 that, just like the plug housing 20, can be made from stainless steel or another metal, and a sealing element 40 that can be made, for example, from a material, such as, a suitable plastic, that can deform sufficiently elastically and/or plastically.

The screw-shaped plug housing 20 has a thickened head part that is provided with knurling 21 on the outer periphery and that is adjacent to the threaded part provided with a thread 22. The plug housing 20 has a central hole with a step-like profile in the embodiment shown, wherein the inner diameter of the hole in the front region of the threaded part is only slightly larger than the outer diameter of the plug capillary tube 10 held in the central hole. The plug capillary tube 10 passes with its front end through the central hole of the plug housing 20, wherein the pressure piece 30 is arranged, radially around the plug capillary tube 10, in front of the plug housing 20 toward the end of the plug capillary tube 10. In its rear region, the outer diameter of the rotationally symmetric pressure piece 30 corresponds to the inner diameter of a receptacle opening 53 of the bushing unit 5 in its rear region facing the plug unit 3. The outer diameter of pressure piece 30 must be somewhat smaller than the inner diameter of the receptacle opening 53, because otherwise the pressure piece may become jammed in the thread 52. The outer diameter of pressure piece 30 should be as large as possible, however, so that the pressure piece is oriented in the axial direction on the plug housing as much as possible, and the hole of the capillary tube 10 and the opening of a bushing capillary tube 57 are aligned as well as possible, in order not to interfere with the flow. The outer diameter of the front region of the pressure piece 30 corresponds to the inner diameter of the receptacle opening 53 in its inward directed, cylindrical end region 56 that is closed off by the bottom wall 51 into which opens the bushing capillary tube opening 55 of the bushing capillary tube 57. This outer diameter likewise must be somewhat smaller than the inner diameter of the cylindrical end region 56 of the receptacle opening 53, so that the assembly and disassembly are not hindered.

The sealing element 40, which has an annular construction, is arranged on the capillary tube in front of the pressure piece 30 toward the end of this plug capillary tube 10.

The end of the plug capillary tube 10 has a constantly increasing outer diameter by means of which a force-receiving region 11 is formed.

The maximum outer diameter of the force-receiving region 11 is less than the inner diameter of the receptacle opening 53 in its inner, cylindrical end region 56 that is delimited by the bottom wall 51. The outer diameter of the sealing element 40 essentially corresponds to the inner diameter of this cylindrical, inner region of the receptacle opening 53.

In its front region facing the force-receiving region 11, the inner diameter of the sealing element 40 is formed essentially complementary to the contours of the outer diameter of the force-receiving region 11, so that the sealing element 40 can be pushed onto the force-receiving region 11 without a large pressure or without a large axial force. The contour of the inner diameter in the front region of the sealing element 40 is, however, advantageously constructed so that the pressureless sliding onto the force-receiving region 11 can take place only up to an axial position in which the end face of the sealing element 40 is still set back by a certain amount relative to the end face of the force-receiving region 11 or plug capillary tube 10.

For assembly of the plug unit 3, the plug housing 20, pressure piece 30, and sealing element 40 can be slid from the front onto the plug capillary tube 10, which in this case still has no force-receiving region 11 enlarged in the radial direction. The force-receiving region 11 can then be produced with a suitable tool, for example, by compression or the like.

As far as this is possible, the force-receiving region 11 of the plug capillary tube 10 could also be produced in advance, and in this case, the remaining components of the plug unit 3 could be slid onto the capillary tube from the other end of the plug capillary tube 10.

Figure 6:
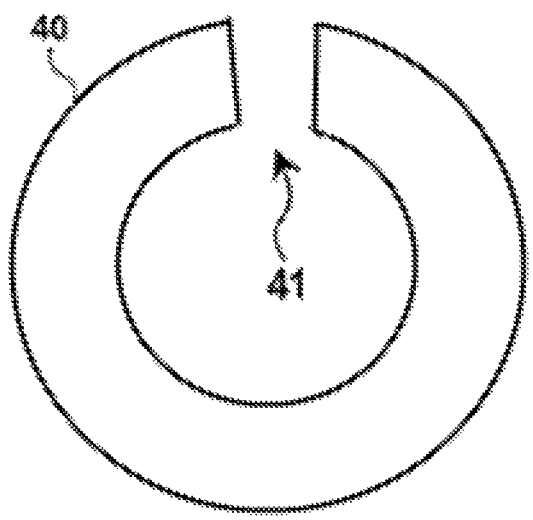
FIG. 6 shows a side view schematic diagram of a slotted annular element embodiment of sealing element 40 according to another embodiment.
Figure 7:
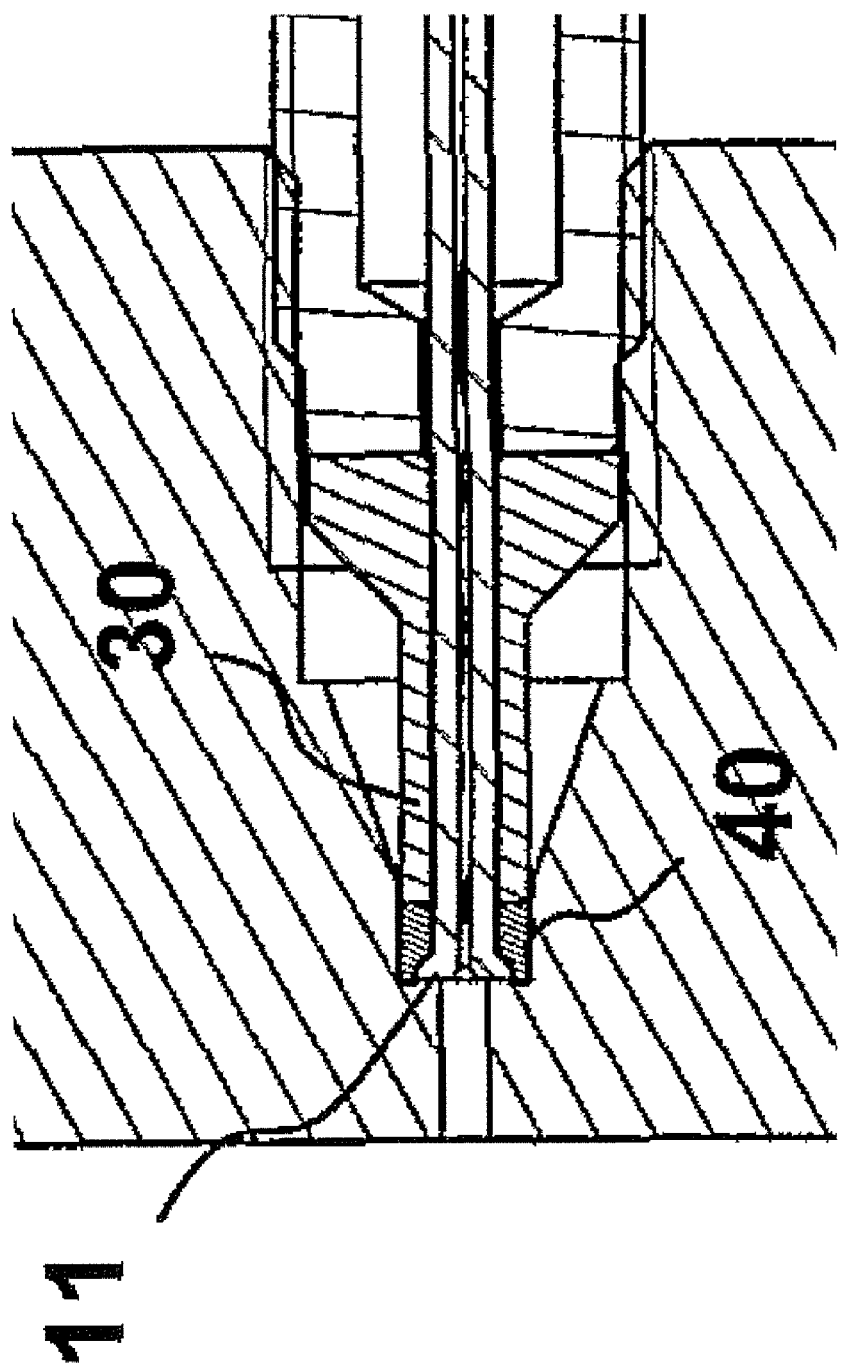
FIG. 7 shows an enlarged illustration of a region of the connection system according to FIG. 2.

The sealing element 40 could also be constructed as an annular element slotted in the axial direction, such as the sealing element 40 shown in FIG. 6, having slot 41, so that the sealing element 40 can then be pushed forward past the enlarged force-receiving region 11 onto the plug capillary tube 10, or can be placed on the plug capillary tube 10 from the side. For this purpose, the material of the sealing element 40 must obviously have sufficient elasticity.

After sliding the components 20, 30 and 40 onto the plug capillary tube 10 and the production of the force-receiving region 11, the plug unit 3 could then be inserted into the bushing unit 5.

The insertion takes place in a simple way in that the plug housing 20 is slid forward without force onto the capillary tube 10 toward the force-receiving region 11, until the pressure piece 30 and the sealing element 40 are moved into their non-pressurized, front position. Subsequently or simultaneously, the plug unit 3 is introduced into the receptacle opening 53 of the bushing unit 5 and the thread 22 of the threaded part of the plug housing 20 is screwed into the inner thread 52 of the receptacle opening 53. During the screwing-in process, the front end face of the plug housing 20 exerts an axial force via the pressure piece 30 onto the sealing element 40 that exerts, for its part, axial force via the force-receiving region 11 onto the plug capillary tube 10. In this way the plug capillary tube 10 is pressed with its end face butted against the bottom wall 51 of the receptacle opening 53, wherein the centering of the plug capillary tube 10 in the inner, cylindrical region of the receptacle opening 53 is guaranteed by means of the sealing element 40 and the front region of the pressure piece 30. The axial force exerted via the pressure piece 30 onto the sealing element 40 is increased through further turning of the plug housing 20 into the bushing housing 50 of the bushing unit 5. During its elastic and/or plastic deformation, the sealing element 40 transmits corresponding pressure forces onto the force-receiving region 11 and the bottom wall 51 in the bushing housing 50 as well as onto the cylinder wall of the cylindrical inner part of the receptacle opening 53. A corresponding good sealing effect is produced in this way, wherein very high pressure forces can be exerted onto the sealing element through merely minimal forces for turning the plug housing 20 into the bushing housing 50.

Figure 2:
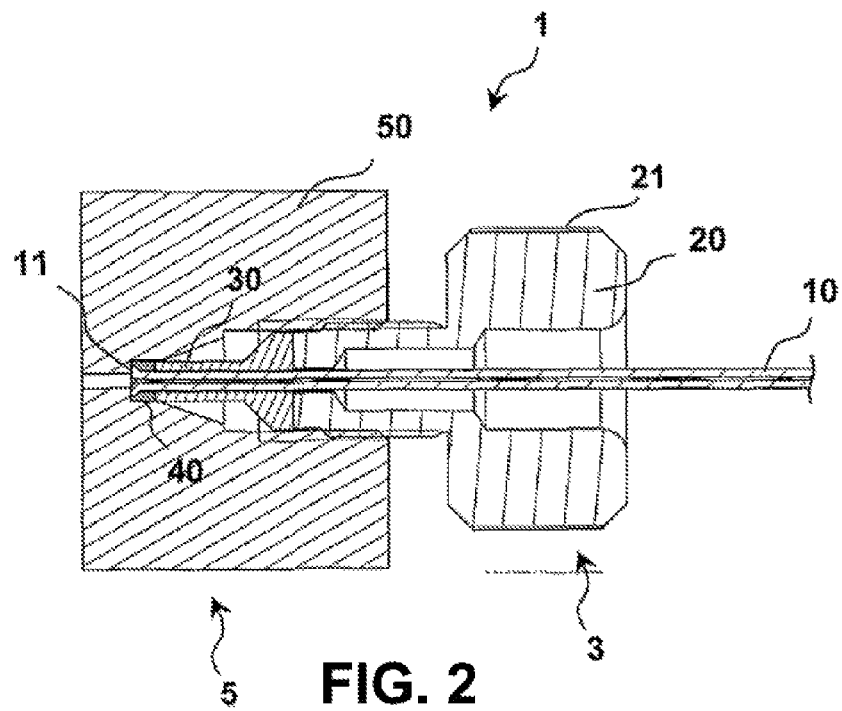
FIG. 2 shows a diagram of the connection system according to FIG. 1, in the assembled state.

From the diagram in FIGS. 1 and 2, it is easily seen that, for different outer diameters of plug capillary tubes 10, pressure pieces 30 or sealing elements 40 must be used that are simply adapted according to their inner diameter, while the plug housing 20 can remain the same, assuming that the central hole in the front region of the threaded part 22 is large enough to receive the relevant plug capillary tube 10.

Different depths of receptacle openings 53, which could vary depending on tolerances or manufacturers, could also be compensated, provided that the threaded part 22 of the plug housing 20 has a sufficient length in the axial direction.

The construction of a plug unit 3 shown in the drawing also guarantees, for different depths of the receptacle opening 53 of the bushing unit 5, that the end face of the plug capillary tube 10 is always positioned with a defined force against the bottom wall 51 of the receptacle opening 53.

For disassembly of the connection system 1, the plug housing 20 need only to be unscrewed from the bushing housing 50 and the plug capillary tube 10 pulled out from the receptacle opening 53 together with the pressure piece 30 and the sealing element 40. The diameter increase in the region of the force-receiving region 11 of the plug capillary tube 10 reliably guarantees that the sealing element 40 does not remain in the receptacle opening 53, especially in the inner, cylindrical region, when the plug capillary tube 10 is pulled out, which would then require it being removed in a laborious way. If the plug unit 3 is then to be installed again, possibly in another (similar) bushing unit 5, then the sealing element 40 can also be exchanged.

If it is not possible, as described above, to push a new sealing element past the force-receiving region 11 onto the capillary tube (or to push on the plug unit 3 from the other end of the plug capillary tube 10), the front-most end of the plug capillary tube 10 with the force-receiving region 11 can optionally be cut so that a new force-receiving region 11 can be produced after new components that are required for the plug unit 3, especially a new sealing element 40, are slid on.

As the material for the sealing element 40, for example, PEEK or a material with suitable chemical and physical properties can be used.

Figure 3:
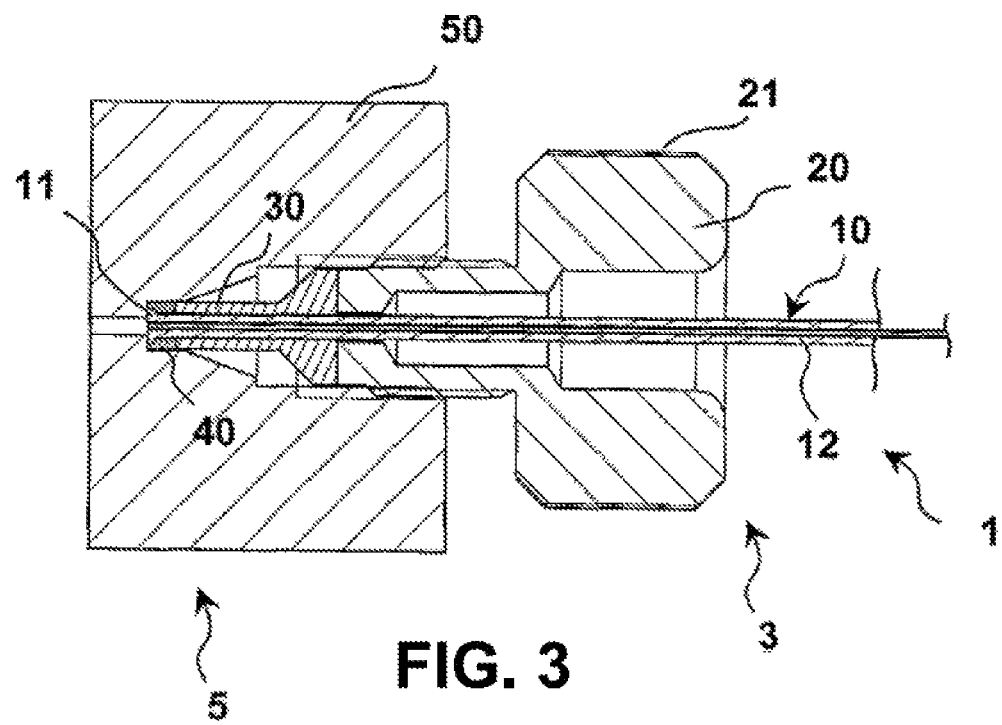
FIG. 3 shows a diagram of another embodiment of a connection system according to the invention with a plug capillary tube consisting of two jacket layers, in the assembled state.

FIG. 3 shows a diagram of another plug unit 1 in the assembled state similar to FIG. 2, wherein the plug capillary tube 10 has an outer jacket layer 12 that is made from a material that can deform slightly plastically, and that surrounds an inner jacket layer. The outer jacket layer can be made, for example, from plastic that can deform thermally, while the inner jacket layer is made from a material, for example, stainless steel, glass, fused silica, or another plastic, which is suitable for conducting the relevant liquid. These materials are obviously also suitable for a plug capillary tube 10 that has a wall made from only a single material (cf., e.g., the embodiment shown in FIGS. 1 and 2).

In the embodiment according to FIG. 3, the inner jacket layer could also project beyond the front part of the outer jacket layer 12 deformed into a trumpet-like shape wherein, in the installed state of the plug unit 1 this projecting part can reach into the part of the channel formed in the bushing housing for the liquid to be conducted adjacent to the force-receiving region 11 of the front region 56 of the receptacle opening 53. Thus, for the production of the part of the plug capillary tube 10 enlarged like a trumpet, a front sub-region of the outer jacket layer 12 can be pushed back and deformed plastically. However, in this way there is the disadvantage that a dead volume not carrying a flow is produced between the front end of the inner jacket layer and the force-receiving region 11, if the outer diameter of the inner jacket layer does not essentially correspond to the inner diameter of the channel in the bushing housing 50. This means, however, the observance of correspondingly smaller production tolerances, which is associated with corresponding expense. However, it is possible in a simple way to shape the front face of the enlarged front region of the outer jacket layer 12 to be flush with the front end of the inner jacket layer, in that the projecting part of the inner layer is cut so that it is flush after the production of the force-receiving region.

Figure 4:
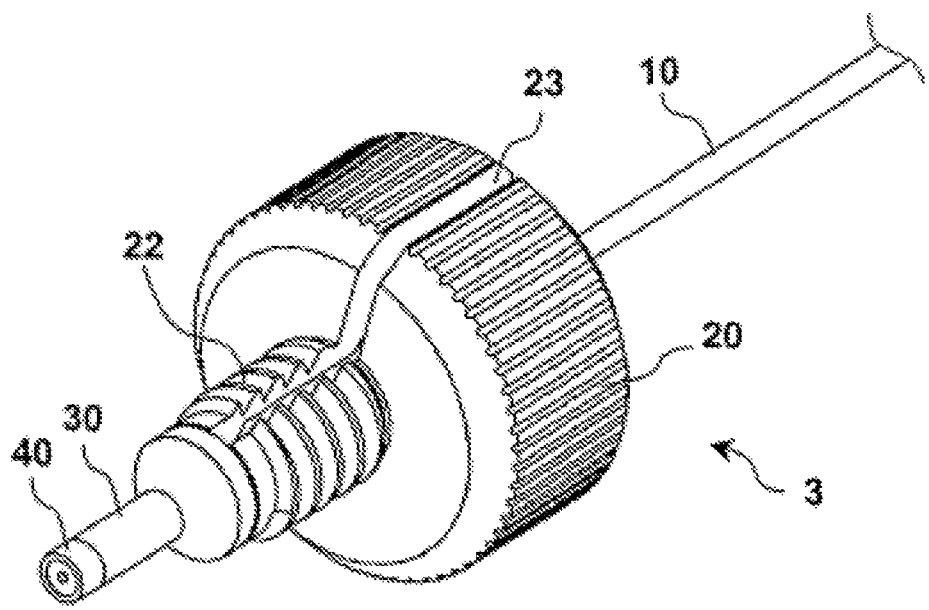
FIG. 4 shows an oblique diagram of a slotted plug unit of another embodiment of connection system that is arranged, together with a pressure piece and a sealing element, on a plug capillary tube for assembly with a bushing unit.

FIG. 4 shows a plug unit 5 in which the plug housing 20 has a radial slot 23 that allows the plug housing 20 to be pushed onto the plug capillary tube 10 from the side, or that allows the plug capillary tube 20 to be inserted via the slot 23 into the coaxial mounting position within the plug housing 20 provided for this purpose. This simplifies the assembly or disassembly as well as the exchange of the plug housing 20.

Figure 5:
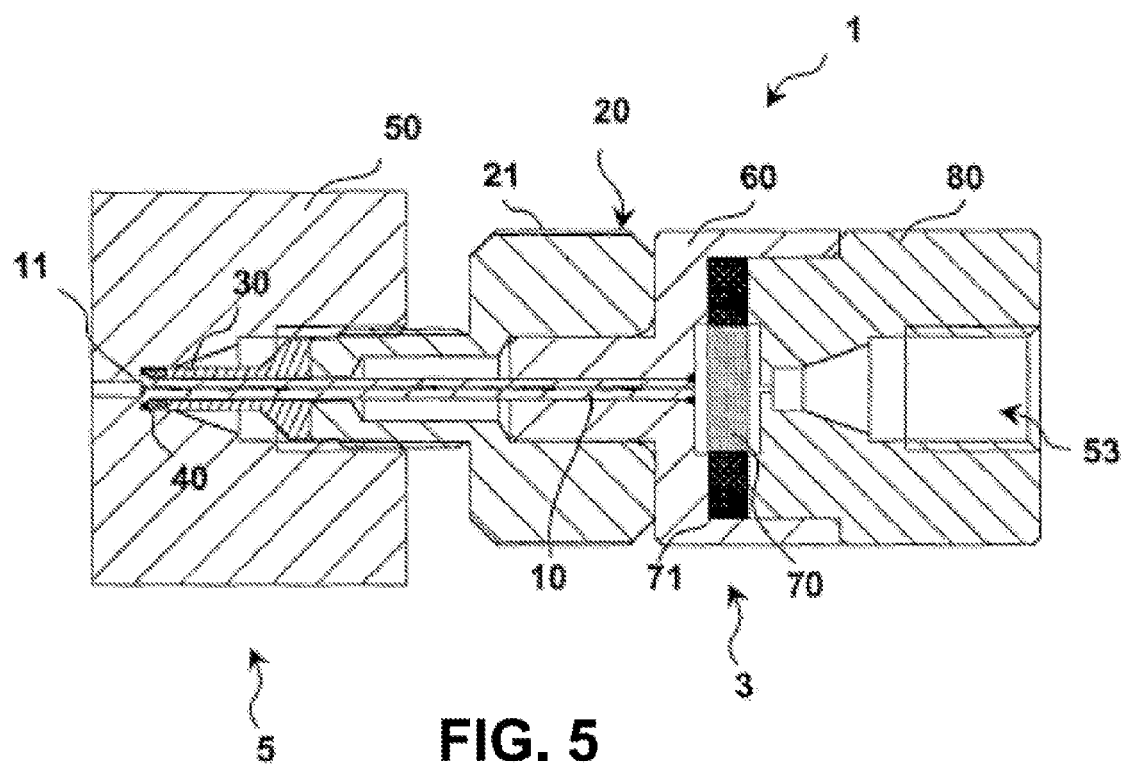
FIG. 5 shows an embodiment of a connection system in which the plug unit is expanded by a housing with a two-part construction in which a filter is provided.

FIG. 5 shows an embodiment of a connection system 1 in which the plug unit 5 is expanded by a housing 60, 80 that has a two-part construction and in which a filter (or a fritted filter) 71 is provided. The first, pot-shaped housing part 60 holds the disk-shaped filter 71 whose radially outer edge region is held between the end face of the second housing part 80 and the floor of the first, pot-shaped housing part 60. The outer edge region simultaneously takes on a sealing function, and for this purpose can be formed from a suitable material. The radially inner region of the filter 71 represents the actual filter region 70, and can be constructed in a known way for this purpose. The second housing part 80 is constructed in its rear region as the bushing housing 50, and features a corresponding receptacle opening 53.

The front region of the first housing part 60 engages in the rear recess in the plug housing 20, wherein the plug housing 20 and the housing part 60 are preferably constructed so that they are connected to be axially rotatable relative to each other. This can be effected, for example, by a connection of the parts locking in the axial direction. In this case, the plug capillary tube 10 is advantageously connected rigidly and tightly to the housing 60, 80, especially to the first housing part 60, for example, through fusion, wherein the channel of the plug capillary tube 10 is connected fluidically with the receptacle opening 53 in the second housing part 80 via a through-flow region formed in the housing 60, 80 in which the filter 71 is arranged. The plug capillary tube 10 must then be cut accordingly with respect to length. The rotating connection of the plug housing 20 guarantees that, for the assembly of the entire plug unit 5 (that comprises, in this case, the housing 60, 80 and the fritted filter 71) the capillary tube does not also rotate when the plug housing 20 is screwed into the receptacle opening 53 of the bushing housing.

The simple, tool-free installation of the plug unit 5 into the bushing unit 3 enables the filter to be exchanged or cleaned quickly.

The structural and functional features described above only in connection with one actual embodiment could obviously also be combined with each other to form other possible embodiments.

The above-described illustrative embodiments are meant to illustrate the principles of the invention, but not to limit the scope of the invention. Various other embodiments and modifications to these illustrative embodiments may be made by those skilled in the art without departing from the scope of the present invention.

What is claimed is:

1. A plug connecting to a bushing comprising:
   (a) a plug housing for holding a front end of a plug capillary tube, the plug housing having a central hole and an axial threaded region;
   (b) the plug capillary tube configured to be disposed through the central hole of the plug housing, the plug capillary tube having a force-receiving region with a trumpet shape at the front end, in which the force-receiving region has an outer diameter increasing continuously towards an end face of the plug capillary tube;
   (c) an annular sealing element configured to be mounted on the plug capillary tube towards the end face of the plug capillary tube, the annular sealing element having an inner diameter formed to enlarge along its length toward the end face of the plug capillary tube complementary to contours of the outer diameter of the force receiving region;
   (d) an elongated pressure piece for mounting on the plug capillary tube between the plug housing and the annular sealing element;
   wherein the plug housing is configured to be rotatably and detachably connected to the bushing, the bushing having a receptacle opening to receive the plug, the receptacle opening including a mating thread, in which the mating thread matches the axial threaded region of the plug housing, in which an inward directed portion of the receptacle opening has a cylindrical end region delimited by a bottom wall, in which the cylindrical end region opens to a bushing capillary passage,
   the bushing is configured to receive the front end of the plug capillary tube into the cylindrical end region of the receptacle opening where the end face of the front end of the plug capillary tube is essentially aligned opposite a front end of the bushing capillary passage of the bushing and the end face of the plug capillary tube is against the bottom wall of the cylindrical end region,
   wherein the annular sealing element is configured to seal a radially outward region of the force-receiving region and a cylinder wall of the cylindrical end region so that a dead volume is avoided in the cylindrical end region of the receptacle opening when the plug housing is rotatably connected to the bushing, the plug housing applies an inward axial force to the pressure piece, where a front end face of the pressure piece transmits an axial force without transmitting a friction from the plug housing to the annular sealing element, in which an end face of the annular sealing element applies an axial force on the force-receiving region of the front end of the plug capillary tube.

2. The plug of claim 1, in which the pressure piece comprises
   a first front end having an outer diameter smaller than an inner diameter of the cylindrical end region, and
   a second rear end having an outer diameter that is larger than the outer diameter of the first front end and being smaller than an inner diameter of the receptacle opening.

3. The plug of claim 1, in which a channel opening at the force-receiving region of the plug capillary tube has an inner diameter that is maintained at a same value of the plug capillary tube.

4. A connection system comprising:
   (I) a plug rotatably connected to a bushing, the plug including
      (a) a plug housing having a central hole and an axial threaded region;
      (b) a plug capillary tube disposed through the central hole of the plug housing, the plug capillary tube having a force-receiving region with a trumpet shape at a front end, in which the force-receiving region has an outer diameter increasing continuously towards an end face of the plug capillary tube;
      (c) an annular sealing element mounted on the plug capillary tube towards the end face of the plug capillary tube, the annular sealing element having an inner diameter formed to enlarge along its length toward the end face of the plug capillary tube complementary to contours of the outer diameter of the force receiving region;
(d) an elongated pressure piece mounted on the plug capillary tube between the plug housing and the annular sealing element; and
(II) the bushing having a receptacle opening to receive the plug housing, the receptacle opening including a mating thread, in which the mating thread is rotatably connected to the axial threaded region of the plug housing, in which an inward directed portion of the receptacle opening has a cylindrical end region delimited by a bottom wall, in which the cylindrical end region opens to a bushing capillary passage, the front end of the plug capillary tube is disposed into the cylindrical end region of the receptacle opening where the end face of the front end of the plug capillary tube is essentially aligned opposite a front end of the bushing capillary passage of the bushing and the end face of the plug capillary tube is against the bottom wall of the cylindrical end region,
wherein the annular sealing element pushes the end face of the plug capillary tube against the bottom wall and seals a radially outward region of the force-receiving region and a cylinder wall of the cylindrical end region so that a dead volume is avoided in the cylindrical end region of the receptacle opening when the plug housing is rotatably connected to the bushing, the plug housing applies an inward axial force to the pressure piece, such that a front end face of the pressure piece transmits an axial force without transmitting a friction from the plug housing to the annular sealing element, where an end face of the annular sealing element plastically deforms and applies an axial force on the force-receiving region of the front end of the plug capillary tube.

5. The connection system of claim 4, in which the pressure piece comprises:
   a first front end having an outer diameter smaller than an inner diameter of the cylindrical end region, and
   a second rear end having an outer diameter that is larger than the outer diameter of the first front end and being essentially equal to an inner diameter of the receptacle opening.

6. The connection system of claim 4, in which a channel opening at the force-receiving region of the plug capillary tube has an inner diameter that is maintained at a same value of the plug capillary tube.

* * * * *